United States Patent [19]

John

[11] Patent Number: 4,557,270
[45] Date of Patent: Dec. 10, 1985

[54] ELECTROENCEPHALOGRAPHIC SYSTEM FOR INTRA-OPERATIVE OPEN-HEART SURGERY

[75] Inventor: Erwin R. John, Mamaroneck, N.Y.

[73] Assignee: New York University, New York, N.Y.

[21] Appl. No.: 525,628

[22] Filed: Aug. 23, 1983

[51] Int. Cl.$^4$ ................................................ A61B 5/04
[52] U.S. Cl. ...................................... 128/731; 128/691
[58] Field of Search .............................. 128/731–733, 128/691, 694, 736

[56] References Cited

U.S. PATENT DOCUMENTS

| | | | |
|---|---|---|---|
| 3,696,808 | 10/1972 | Roy et al. | 128/731 |
| 4,171,696 | 10/1979 | John | 128/731 |
| 4,188,956 | 2/1980 | John | 128/731 |
| 4,201,224 | 5/1980 | John | 128/731 |
| 4,214,591 | 7/1980 | Sato et al. | 128/731 |
| 4,254,779 | 3/1981 | Miyata et al. | 128/731 |
| 4,279,258 | 7/1981 | John | 128/731 |
| 4,408,616 | 10/1983 | Duffy et al. | 128/731 |
| 4,417,591 | 11/1983 | Culver | 128/731 |

OTHER PUBLICATIONS

Sotaniemi et al., "Quantitative EEG as a Measure of Cerebral Dysfunction Before and After Open-Heart Surgery", *Electroencephalography and Clinical Neurophysiology*, 1980, 50:81–50:95.

Primary Examiner—Lee S. Cohen
Assistant Examiner—Angela D. Sykes
Attorney, Agent, or Firm—Eliot S. Gerber

[57] ABSTRACT

During open-heart surgery an EEG (electroencephalograph) system detects a patient's brain waves, amplifies the brain wave signals and converts them into digital data. The cardiopulmonary bypass pump (heart-lung machine) is connected to blood flow and blood temperature transducers whose measurements, in digital form, are used to calculate a standard of normal electro-physiological responses to blood flow and temperature changes with which the patient's actual brain wave responses will be compared. A visual display indicates to the surgical team, as to each of eight brain sectors, whether the patient's brain waves show that remedial action may be required. The digitalized brain wave signals, after processing to reduce muscle artifact and other noise, are displayed, in one embodiment, as intensity modulated time segments, using a moving window type of display in which the current segment is statistically compared to the group of immediate prior segments to provide a current self-norm (NORMS n). A new display (NORMS n+1 is started when a statistically meaningful different segment occurs and comparison is made and displayed between the two displays (NORMS n+1 and NORMS n). In another embodiment the same comparison of the groups is made, but the visual display utilizes a set of color-coded lights in the eight sectors of the display.

2 Claims, 7 Drawing Figures

ELECTROENCEPHALOGRAPHIC SYSTEM FOR INTRA-OPERATIVE OPEN-HEART SURGERY

BACKGROUND OF THE INVENTION

The present invention relates to medical and surgical apparatus and more particularly to the monitoring of a patient having open-heart surgery by EEG (electroencephalographic) apparatus.

Generally, a carido-pulmonary bypass machine is used in open-heart surgery. A "cardio-pulmonary bypass", i.e., a heart-lung machine, is a mechanical device that assumes the functions of the heart and the lungs for the generally one to four hours of the open-heart surgery. It is a pump and oxygenator which supplies oxygenated blood while the heart is stopped and excluded from circulation. A typical open-heart surgical procedure would be the replacement of the patient's aortic valve, which guards the exit of the left ventricle (cardiac valvular replacement). Due to stenosis (constriction of the valve) it may be repaired or replaced with a plastic, metal, or pig-heart valve.

The medical literature has recognized that cerebral disorders (damage to the central nervous system CNS) may result from open-heart surgical procedures. The studies have indicated that the effect of the disturbed blood flow or metabolism of the brain which may occur during such open-heart surgery may be detected by comparing the patient's EEG (electroencephalographic) examination made before the operation with the EEG examination conducted after the operation. See Sotaniemi et al "Quantitative EEG As A Measure Of Cerebral Dysfunction Before And After Open-Heart Surgery", *Electroencephalography and Clinical Neurophysiology*, 1980, 50:81–95.

The number of open-heart surgical procedures has risen dramatically in recent years and it is presently estimated that more than 100,000 of such operations may be performed each year. Studies have also indicated that the heart valve replacement operation, which is a widely used open-heart surgical operation, has a comparatively beneficial effect on long-term patient life compared with alternative procedures such as drug regimes. Coronary artery bypass operations, while not yet demonstrated to increase longevity, often improve the quality of the life by decreasing angina pains and limitations on physical activity. Such surgery is being performed at a steadily rising rate.

The present invention is based upon recent findings that certain brain wave information, which may be obtained and specially processed during the open-heart surgical operation, provides a sensitive indication of the progress of the operation and whether remedial steps are immediately required. More specifically, the brain wave information which may be obtained and analyzed simultaneously and on-line with the open-heart operative procedure may be used as an indication of whether the blood flow from the heart-lung machine should be increased or decreased, or whether other measures should be taken to prevent damage to the brain.

Generally, during an open-heart operation it is necessary to decrease the artificial heart pump pressure in order to sew connections to the valves and blood vessels. It is critical, however, that the blood pressure not drop so far, or for such a prolonged period of time, as to bring on cerebral disorder because of lack of oxygen to the brain or disturbances in the brain metabolism. Monitoring of the brain waves during the operation may provide a sensitive indication of the required blood flow so that it does not drop below the critical amount for the critical time period. This is a complicated matter since the blood flow requirement of each individual varies depending upon his or her weight, age, physical condition and metabolism. What may be a sufficient blood flow during open-heart surgery for one patient may be insufficient for the next.

OBJECTIVES AND FEATURES OF THE INVENTION

It is an objective of the present inventon to provide for intra-operative EEG monitoring of patients during cardiac surgery involving cardio-pulmonary bypass (CPB).

It is a further objective of the present invention that the system be sufficiently simple and reliable in operation and in its presentation of information to the surgical team so that it may be used without complications or confusion.

It is a further objective of the present invention to provide an EEG system for use during such cardiac surgery which will help prevent under perfusion, brain damage, cerebral anoxia or other disorders which might arise from such surgery.

It is a feature of the present invention to provide a novel EEG system for use in intra-operative open-heart surgery. The system has blood flow and blood temperature measuring instruments (transducers) connected to the cardiopulmonary bypass (heart-lung machine). The novel EEG system takes account of the electro-physiological responses to changes in blood flow and temperature observed during open-heart operations in a group of patients with *normal outcome*. These normal responses are reflected in a "pump-patient relationship". The system compares the EEG response of the normal outcome group under the conditions of blood flow and temperature, which the patient is presently experiencing, with the actual responses reflected in the patient's on-line EEG data, to determine abnormal responses which may indicate the necessity for changes in the operative parameters, such as increasing the pump pressure.

It is a further feature that a simplified and readily comprehended visual display be presented to the surgical personnel of the patient's on-going brain activity during the open-heart surgery. The display presents, as to each of the eight brain sectors, a moving window type of histograph. A set of brain wave data forms a group of time segments, for example, 24 segments, which is compiled, displayed and statistically compared, as a group, with the next occurring time segment of brain wave data and with the normal outcome data under similar flow and temperature. The oldest segment is removed from the group and the latest segment added. The EEG data is processed so that segments containing muscle artifact, or other noise, are excluded from these comparisons. The statistical comparison and visual display provides an immediate and apparent indication whether the current brain wave segments are meaningfully different from the patient's own on-going prior set of brain wave EEG segments or from the average data observed in the normal outcome group under the same conditions.

It is a still and further feature of the invention that, in an alternative embodiment having a simplified visual display, a set of color-coded lights are used on a panel having a head outline divided into eight sectors. The same statistical data processing occurs, comparing a moving group of 24 segments with the next segment and then with the next group of segments, as well as with the normal outcome data. For example, for each head sector the light is green when the comparison shows no meaningful change; the light is amber when the next segment is meaningfully different from the current group or normal outcome data; and the light is red when the new group is meaningfully different from the prior group, or from normal outcome data.

BRIEF DESCRIPTION OF THE DRAWINGS

Other objectives and features of the present invention will be apparent from the following detailed descprition which should be taken in conjunction with the accompanying drawings.

In the drawings.

DETAILED DESCRIPTION OF THE INVENTION

Figure 1:
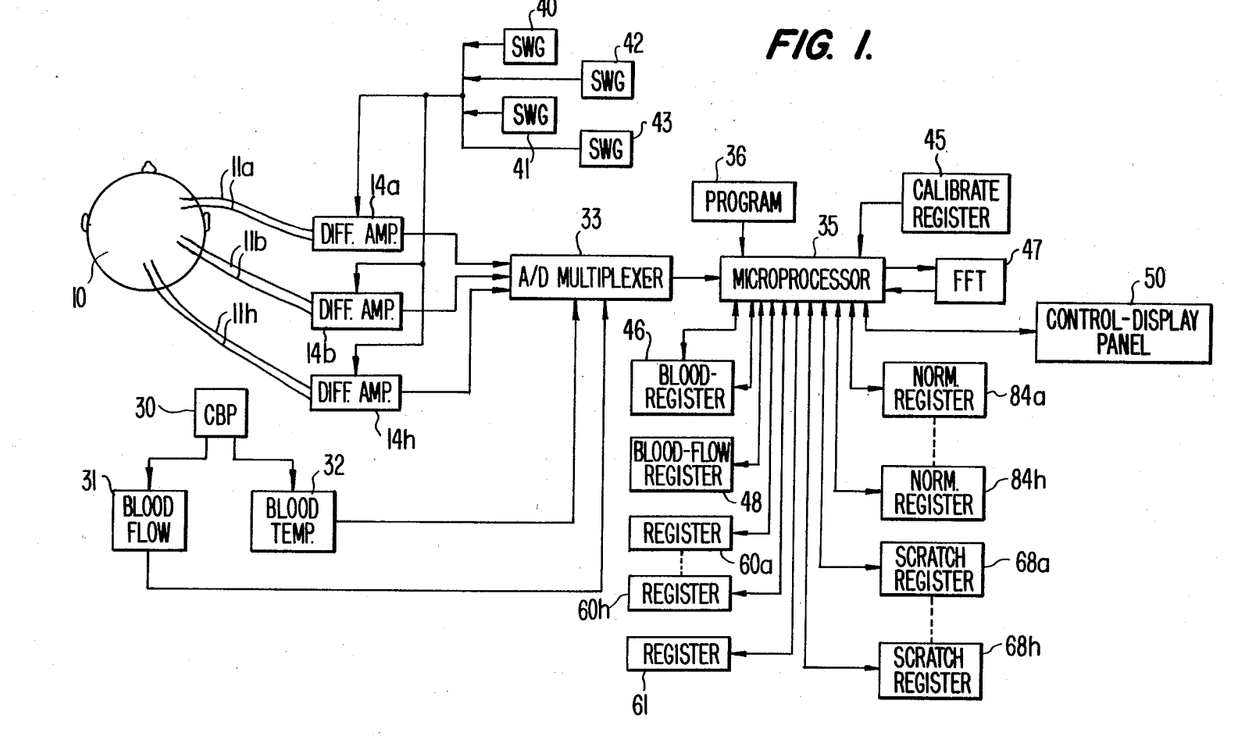
FIG. 1 is a block schematic diagram of the EEG system of the present invention.
Figure 2:
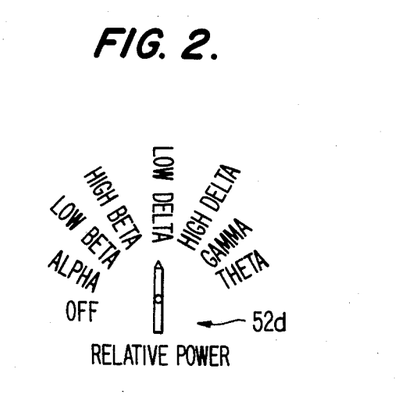
FIG. 2 is a front plan view of a portion of the control panel of FIG. 3.

As shown in FIG. 1, the apparatus of the present invention is described in connection with the block diagram of FIG. 1 showing the various components of the system. The patient who is to be operated upon should be analyzed as to his brain wave functioning before the operation, during the operation, and after the operation. Essentially the same apparatus may be used at all three times with, however, proper modifications for use before and after the operation.

The system of FIG. 1 will be described primarily in connection with its use during the surgical operation. It will be described, in certain places, in terms of an artery bypass open-heart surgical procedure. However, it will be understood that other open-heart or vascular surgical procedures, or even general surgery, will benefit from using the apparatus of the present invention.

As shown in FIG. 1, the head 10 of the patient is connected to a set of electrodes. The conventional EEG International 10/20 electrode system and nomenclature is preferably used. Only three pairs of electrodes 11a, 11b and 11h are shown in FIG. 1 so as to simplify the drawing. However, preferably 16 electrodes (8 pairs) are used to provide 8 bipolar derivations. The preferred derivations would be $F_7 T_3$, $F_8 T_4$, $T_3 T_5$, $T_4 T_6$, $C_3 C_Z$, $C_4 C_Z$, $P_3 O_1$ and $P_4 O_2$. Further information regarding the use of pair derivations may be obtained from the inventor's prior patent entitled "System And Method For Electrode Pair Derivations In Electroencephalography", Ser. No. 873,118, U.S. Pat. No. 4,411,273, incorporated by reference herein.

Each of the pairs of electrode leads 11a–11h, preferably eight pairs of such leads, in connected to its own individual differential amplifier. As illustrated, the electrode pair 11a is connected to the amplifier 14a, the electrode pair 11b is connected to the amplifier 14b and the electrode pair 11h is connected to the amplifier 14h. As shown, preferably there are eight differential amplifiers 14a–14h.

Each of the differential amplifiers 14a–14h has an input isolation switch to protect against current leakage; for example, a suitable isolation switch is a photo-diode-light-emitting diode (LED) isolation coupler. In addition, each amplifier input is protected from electrical interference by use of a radio-frequency filter and a 60-cycle notch filter. Preferably, each amplifier has a frequency range of 0.5 to 100 Hz, gain of 10,000, a common mode rejection of 160 DB, and noise of less than 2 microvolts. Such high-gain low-noise differential amplifiers are presently commercially available.

An alternative to the use of the eight bipolar derivations would be the direct use of the 19 electrodes of the monopolar International 10/20 system as inputs to 19 corresponding individual amplifiers. Each of the 19 inputs may be compared (referenced) against an inactive electrode such as an electrode connected to the earlobe.

The cardio-pulmonary bypass pump 30, which is a type of artificial heart-lung machine, is used in place of the heart and lungs of the patient during the operation to pump blood and to supply the blood with oxygen. Two on-line measuring transducers are connected to the pump 30. The blood flow transducer 31 provides an electrical output which corresponds to the blood flow in milliliters per minute. The temperature transducer 32 provides an electrical output corresponding to the patient's blood temperature as it flows through the pump 30.

An analog-to-digital multiplexer (A/D multiplexer) 33 provides a digital output from the various analog amplifiers and transducers which are connected to its input. The eight differential amplifiers, represented by 14a–14h are connected to the A/D multiplexer 33, as is the blood flow transducer 31 and the blood temperature transducer 32. The A/D multiplexer 33 samples the EEG waves (outputs of differential amplifiers 14a–14h) at a rate which is compatible with the bandwidth of those amplifiers, preferaby at the rate of 200 to 300 times per second to comply with their 0.05 to 100 Hz bandwidth. The sampling rate applied to the blood flow and blood temperature transducers would be at a lower rate.

In addition, other transducers may provide electrical information concerning the patient which may be sampled at an appropriate rate by the A/D multiplexer 33. For example, measuring transducers may be used whose output lines provide signals indicating body core temperature (thermistor), the patient's blood pressure, the electrocardiogram (EKG) and other patient parameters.

The information from the multiplexer is provided over line 34 to a microprocessor 35. The microprocessor has been programmed by an external software program means such as a floppy disk recorder or other input system 36. The microprocessor may be the INTEL 8086, NEC-PD8086 or the LSI 11-23, or other comparable devices.

The program and its controlled microprocessor condition the input signal and insure that they are valid biological signals. Such validity checks on the input signals include calibration and impedance measurements.

CALIBRATION AND IMPEDANCE TEST

A preferred calibration system utilizes four sine wave generators 40-43 whose outputs are connected to each of the differential amplifiers. The generators produce sine waves at predetermined frequencies, perferably at 2.5, 5.5, 10 and 15.75 Hz. The sine waves suitably are at 20 microvolts peak-to-peak voltage and are mixed into a composite signal over a predetermined time period, for example, 5 seconds of the component signals are fed into each of the differential amplifiers. The composite sine wave signal is amplified by each differential amplifier, converted to a digital set of values by the A/D converter, subjected to spectral analysis and the results transferred to relative power, i.e., what is the percent of the power in each frequency interval. The relative power is then compared to the relative power calibration standard which has been predetermined and stored in the storage register 45. Preferably, the results of the relative power comparison for each channel (each differential amplifier) should be within plus or minus 5% of the unexpected value at each frequency. The operator calibrates by using button 56a on control-display panel 50, see FIG. 3. If the calibration shows an out-of-limit (non-calibrated) amplifier or a defect in the analysis system the warning light 56 will become lighted.

Figure 3:
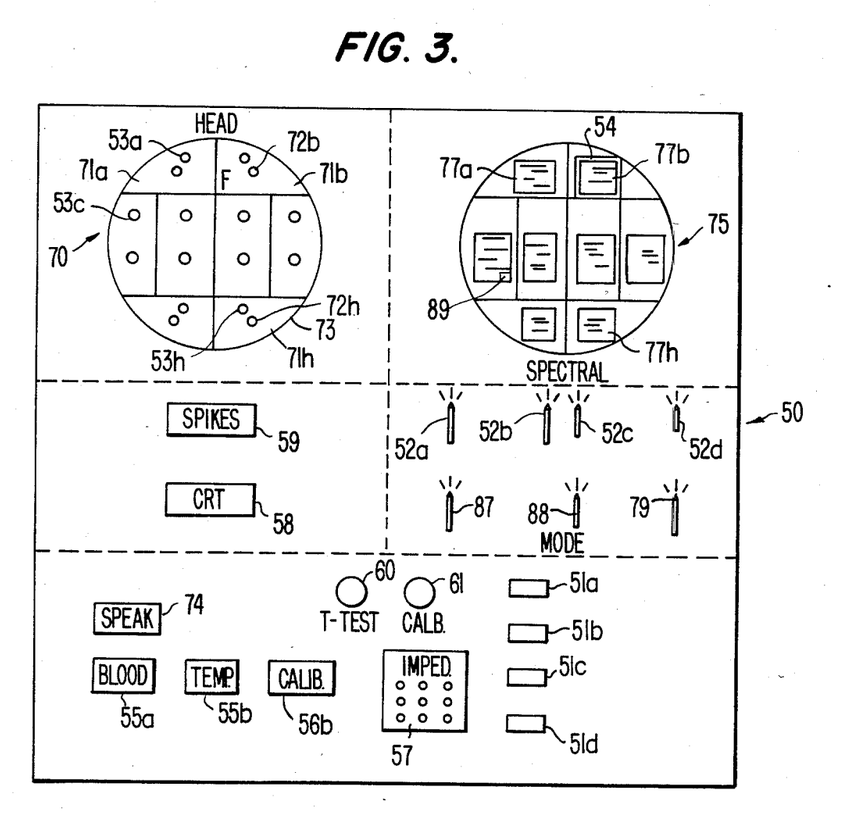
FIG. 3 is a front plan view of the proposed control and display panel for use in the system of FIG. 1.

As explained in the applicant's prior U.S. Pat. No. 4,411,273 (Ser. No. 873,118), the impedance of each of the pairs of electrodes 11a-11h is automatically tested from time to time to ensure proper connection to the patient's scalp. Unacceptable high electrode impedance are reported by the warning lights 57.

MUSCLE ARTIFACT AND SPIKE DETECTION

The system will also provide a means of detecting muscle artifact and epileptiform spikes. The objective is to cancel, i.e., not use, those periods of brain wave activity which are contaminated with muscle or movement artifacts, which appear as noise relative to the desired brain wave signals, but to accept as valid those segments which contain signs of pathology. The number of brain wave spikes may be counted to provide useful information about epileptiform activity due to ischemia which may produce seizures and indicate the risk of brain damage.

In order to detect spikes and muscle artifact, six computations are dynamically performed on each EEG segment. These six computations are as follows:

Mean amplitude ($\overline{V}$), standard deviation of mean amplitude ($\sigma\overline{V}$), mean slope ($\overline{V}'$), standard deviation of mean slope ($\sigma\overline{V}'$), mean sharpness ($\overline{V}''$), and standard deviation of mean sharpness ($\sigma\overline{V}''$). [$V'$ denotes $dV/dt$, and $V''$ denotes $d^2V/dt$ and sigma $=\sigma$).

After these six computations are dynamically computed, for each EEG segment in each derivation, confidence intervals are set for statistically significant deviations from Gaussianity (normal or bell-curve distribution). Reasonable definitions of such confidence intervals are $\overline{V}+3\sigma$, $\overline{V}'+5\sigma$ or $2\mu V/ms$, $\overline{V}''+6\sigma$. However, other confidence intervals may be found preferable during special conditions of anesthesia or CPB.

An estimate of a reliable sample size is preferably made as follows:

Under stable baseline physiological conditions, the system will take successive 2.56 second samples and perform the six computations, described in the paragraphs above, upon integer multiple samples (1, 2, 4 and 8 samples). The values of the 6 parameters ($\overline{V},\overline{V}'$, $\overline{V}''$, $\sigma v$, $\sigma v'$, $\sigma v''$) will be compared, within each derivation, as the sample size is increased, i.e., AS 1,2,4, etc. such samples are combined, until these values stabilize. Stabilization will be defined as a t-test which is not significant between two successive parameter sets, i.e.

$$\frac{\overline{V}_1 - \overline{V}_2}{|\sigma v_1^2 + \sigma v_2^2|^{\frac{1}{2}}} ; \frac{\overline{V}_1' - \overline{V}_2'}{|\sigma v_1'^2 + \sigma v_2'^1|^{\frac{1}{2}}} ; \frac{\overline{V}_1'' - \overline{V}_2''}{|\sigma v''^2_1 + \sigma v''^2_2|^{\frac{1}{2}}}$$

The system will then notify the operator as to the size of a "reliable sample" under current conditions. This will determine the minimum update time during monitoring. Data will continue to be gathered in 2.56 segments, combined to achieve the required size, and the test parameters derived from the "reliable sample" size will be applied to evaluate each such reliable size segment.

If, in any of the six derivations, the voltage value $V_t$ for any time point exceeds $\overline{V}+3\sigma$ or the slope $V'_t$ exceeds $\overline{V}'+5\sigma$, the segment will be considered "suspect". The "reliable sample" waves are displayed on CRT display 58.

For any time point a "suspect" segment will contain a "spike" if it (i) contains a component whose sharpness $V_t''$ exceeds $\overline{V}''+6\sigma$, (ii) contains a component whose rising and falling slope $V'$ exceeds $\overline{V}'+5\sigma$ or $2\ \mu V/ms$, (iii) contains such a component whose duration lies between 10 and 80 ms from the time its amplitude $V$ exceeds $\overline{V}+2\sigma$ until it returns to $\leq \overline{V}+2\sigma$, and (iv) does not contain another such component within 200 ms. Events occurring within 200 ms of the beginning and end of each segment must be disregarded.

The display, on the display panel 50, shown in FIG. 3, includes a spike counter 59, which is a numerical digital display which accumulates total number of spikes in each region.

Unless all of the conditions as to a "spike" are satisfied by the detected suspect segment, the departure from Gaussianity (bell curve) will be interpreted as either muscle artifact (MA) or movement artifact, and the segment will be rejected. If *all* the conditions for a "spike" are satisfied, or if none of the above conditions are detected, the segment will be classified either as an acceptable EEG signal containing an epileptiform spike or an acceptable EEG signal containing no paroxysmal episode. In either case, the segment is accepted for further processing.

DATA ANALYSIS

A "derivation" is the data in one channel, i.e., from one differential amplifier, and a "derivation segment" is the data collected over a period of time (minimum 2.56 seconds; max. 25.6 seconds) for a reliable sample. "Update time" depends on reliability of data.

If any derivation segment from any of the eight derivations is rejected, as artifact, the entire segment (all derivations) is rejected. If all the segments are accepted (all eight derivations), evaluation of the valid biological data continues as follows:

For each accepted segment i recorded from all 8 derivations, the digitized data will be stored in individual scratch registers 60a-60h. Assuming a sampling rate of 200/sec and a maximum segment length of 25.6 sec. with the storage capacity of each scratch register 60a-60h being 5128 words then for the 8 derivations 41.024K words of memory will be occupied per raw segment. Each word is 1–3 bytes, depending upon the microprocessor which is used.

For each "derivation segment", a flag bit (an output signal) will be raised if a spike was detected. The spikes will be counted and displayed on the visual display 50 at digital counter 59.

A Fast Fourier Transform (FFT) will be performed on each derivation segment, preferably using an FFT chip 47.

The actual power spectral values yielded by the FFT of each derivation segment, between 0–100 Hz, will be stored in a series of scratch registers 68a–68h, each of whose size may be 2.4K (coefficient, sine, cosine terms for each frequency×8 derivations).

The absolute power and the percentage of relative power is computed for the following brain wave frequency bands: low delta (0.5–1.5), high delta (1.5–3.5), theta (3.5–7.5), alpha (7.5–12.5), low beta (12.5–25), high beta (25–50) and gamma (50–100) (all in Hz). The power data are subjected to Z-transformation; for each feature the differences between the patient's values and the mean for the normal group is divided by the standard deviation of the normal group. The Z-transformation method characterizes the deviation of the subject value from the normal outcome mean value (or any other norm which is selected) as a number of standard deviations (error steps). The "normal group" is the normal outcome group.

The formula is:
$$Z = (X - M)/\sigma X$$

where the number of error steps, Z, is representative of a particular neurometric invariate or multivariate index and equal to the difference between the patient's index value for that feature, X, and the group mean value, M, divided by the standard deviation of the whole sample, $\sigma_x$. The total sample standard deviation is computed according to:

$$\sigma_x = \sqrt{\Sigma(x - \bar{x})^2}$$

where X is the patient index value and $\bar{x}$ is the average index value of the control group.

The effect of the Z-transform is to provide the common metric of relative probability as the dimensions or units in which all features are stated. Relative probability means the probability of obtaining the observed value by chance in a member of the control group.

A set of thresholds, based on selected norms, is established; for example, a norm is established by evaluation of a group of cardiovascular surgical patients (control group), whose post-operative recovery was without neurological complications, under representative conditions of premedication, anesthesia and CPB. The set of norms provides the criteria for what is considered to be "abnormal" low delta, high delta, theta, alpha, low beta, high beta, high gamma, in absolute power and relative power.

The norms which may be selected include—but are not limited to:

(1) population norms—age regression equations for the normal unanesthesized patient (used for preoperative screening);

(2) self-norms obtained from the individual patients before anesthesia and before the operation (used as a comparison to assess the anesthetic procedure or the effect of non-pulsatile flow at normal flow rates and temperature);

(3) post-anesthetic and pre-operative (used to assess the effect of the anesthetic and the patient's non-pulsatile flow at normal flow rates and temperatures); these are self-norms;

(4) the patient's self-norms after being anesthesized and while on the heart machine (CPB) (used to assess the effect of non-pulsatile flow); the CPB is at normal flow and temperature;

(5) "pump patient relationship norms" derived from groups of previous patients of approximately comparable age to the present individual patient at each pump flow rate and blood temperature, all of whom displayed no neurological dysfunctions or cognitive/emotional impairment following successful CPB procedures (used to identify brain changes beyond the limits predicted by the "pump-patient relationship" set forth below). The "pump-patient relationship" describes the purely biophysical effects of cardiopulmonary bypass;

(6) population norms for specific intraoperative conditions while using the CPB (to gauge the clinical significance of observed changes). For example, the conditions may include: (a) specific anesthetic agents—the effect of a particular anesthetic agent may be general and different from another anesthetic agent, (b) the reaction to specific changes in pump flow rate and changes in temperature. (rates of changes)

The age-regression equations, population norms and pump patient relationship described above provide the mean (M) and standard deviation ($\sigma$) of every quantitative group of features for a group of persons who are the same age as the patient. They may be either normal healthy unanesthesized subjects or patients who had CPB without subsequent complications. The "self-norms" will be computed as follows:

1. The reliable sample size will be determined by the operation described above;

2. Preferably twenty-four samples of reliable size will be gathered. As each sample is gathered, the measures which have been optionally selected will be quantitatively extracted and stored on the scratch pad memory 61. The raw sample will be deleted;

3. After 24 reliable samples have been gathered, the mean (M) and standard deviation ($\sigma$) of each measure will be computed across the set of 24 samples. These values of M and $\sigma$ will define the self-norm.

The "pump-patient relationship" of the present invention predicts the percent change in neurophysiological processes attributable to the biophysical consequences of reduced blood volume per unit time, and reduced temperature.

$$\% \text{ change} = A \left[ \frac{T_N - T_P}{10} \right] + B \left[ \frac{V_N - V_P}{V_N} \right]$$

where
$T_N$ = normal body temperature, 37° C.
$T_P$ = perfusion blood temperature
$V_N$ = normal perfusion volume
$V_P$ = current pump perfusion volume
A and B are coefficients and fractions required to scale the parenthetical values to appropriate percentages. A is in the range 0.4 to 0.6 and preferably 0.5; B is in the range 0.2 to 0.5 and is preferably 0.4.

The data is also analyzed as to its statistical significance. It is important not only to know how different one group of data is from another, but also what is the likelihood that the difference is meaningful and not just a matter of chance. The "t" test is used to indicate the degree of confidence that the data are not due to chance.

The "t test" or "Students t test" is a statistical test for the measure of the significance of the difference between two sample populations (here, conditions x and y) and provides a selected degree of statistical confidence ("P"). For example, it may indicate a high level of confidence, i.e., that the brain "very likely" responded differently to two stimuli. The "very likely" may be P=0.001, which indicates the result occurring by random chance is 1 in 1000.

The t-test computation is $$t = \left| \frac{\frac{\Sigma x}{N_x} - \frac{\Sigma y}{N}}{\sqrt{\frac{\sigma x^2}{N_x} \frac{\sigma y^2}{N_y}}} \right|$$

where x and y are the two conditions being measured, N is the sample size, $\Sigma$ is the sum and $\sigma x^2 = \Sigma x^2/N_x(\Sigma x)^2/(N_x)$ Absolute total power and relative (percent) power will be computed for each derivation segment in each frequency band (alpha, low beta, high beta, low delta, high delta, gamma and theta). Coherence and symmetry will also be computed for each frequency band between homologous pairs of derivations.

After data reduction, each derivation segment will be evaluated against the selected set of norms (explained above) using one or more of the following options. The options are selected by the switches 52a–52d on display panel 50.

1. Absolute power spectrum, coherence and symmetry (switch 52a);
2. Relative power spectrum, coherence and symmetry (switch 52b);
3. Absolute power (switch 52c) or relative power (switch 52d) in high delta, theta, alpha and beta frequency bands will be tested for whether it is beyond the mean value $\pm 2\sigma$, relative to any selected set of norms.

The "possible abnormality" visual indicator lights 51a–51d will light with each light 51a–51d corresponding to a respective frequency band on the display panel 50 when the contect of any band in any head region is beyond the threshold limit. In addition, an "alarm" light, preferably red LED 53a–53h, will light in a flashing on-off manner in the corresponding head sector. Alternatively, if a full array (window) 77a–77h is displayed its rim 54 will flash on-off in red for an "alarm" signal, see FIG. 3.

It is presently believed that excessive low delta probably reflects muscle movements, excessive high beta probably reflects muscle artifacts, and excessive gamma probably reflects environmental noise which may have eluded the artifact rejection and noise suppression means. Preferably, data of "questionable validity" should be accepted contingently and so indicated by lighting indicators 51a–51d with on-off flashing; while possible non-cerebral sources for the excessively high levels are sought.

DATA DISPLAY

The results of data evaluation are preferably displayed in two ways: (i) normal-abnormal head diagram 70; and/or (ii) intensity-modulated topographic spectral arrays 75.

Normal-abnormal indicators and intensity-modulated spectral arrays may be superimposed as a single display, or may be two separate displays.

A. Normal-Abnormal Head Diagrams

On the instrument panel 50, an outline of a head is depicted seen face upward. The head is divided into eight sectors 71a–71h, with each sector corresponding to each derivation. Each sector 71a–71h contains a light indicator 72a–72h such as an LED (light-emitting diode).

If a current EEG segment for a derivation is evaluated as within normal limits (using options selected in Data Analysis), the indicator LED 72a–72h will be green. If the segment is found to be abnormal, the LED will be red. If a spike, or spikes, was formed in a derivation segment, the corresponding LED will flash red at 1 second intervals. If any derivation is red for 2 successive segments, a tone speaker 74 will beep. If the derivation remains red for more than 1 minute, the pitch of the tone will rise.

B. Intensity-Modulated Topographical Spectral Arrays

On the panel 50, a second head diagram 75 is presented on a black-and-white video screen 76. This idealized head 75 is divided into 8 sectors 77a–77h corresponding to the 8 bipolar derivations (or alternatively the 19 monopolar sectors, if desired). Each sector 77a–77h contains 24 horizontal lines. The "lines" are horizontal stripes (elongated areas). The optimal sample size might be larger or smaller. Each line represents the result of a spectral analysis (FFT) of an EEG segment of reliable size for the patient currently under evaluation. The line may represent the full spectrum, five absolute power frequency bands, four relative power frequency bands, coherence or asymmetry within the four bands or any set of measures selected from the quantitative options on the control panel by the switch 79. These measures are arranged in an orderly way from left to right along the line. The value of each measure is represented on a gray scale, ranging from black, which might correspond to 0 voltage or 0 percent or p=not significant, to white, which might correspond to maximum voltage (calibration scale at side of head) or 100 percent or p=extremely significant, see FIG. 4.

Figure 4:
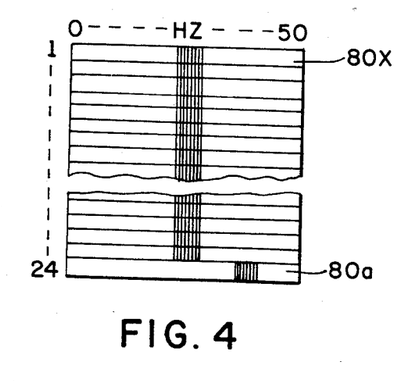
FIG. 4 is a drawing illustrating one of the spectral arrays under a first set of conditions.

For example, as shown in FIG. 4, assume the samples 80a–80x represent the actual power frequency spectrum of reliable EEG segments with each line sample representing a measure of a segment. Each pixel from left to right would represent the actual power found in that EEG sample from 0 to 50 Hz as a shade of grey between black and white. As each sample is acquired and analyzed, it displaces the previous line upward. Thus, if a reliable sample required a 10-second sample, 24 horizontal lines would describe the last 4 minutes of EEG analysis, with the most recent 10 seconds 80a at the bottom of the stack and the oldest sample at the top 80x. This stack 80 of samples represents a window. As each successive segment is recorded and analyzed, it will be evaluated against the set of statistics (the M's and $\sigma$'s which the operator selected as the most appropriate norm). The window moves so that it is "on-line", i.e., includes the most current data. In the example illustrated in FIG. 4, the power in the samples 80b–80x is centered at about 25 Hz while the power in the segment 80a is centered at about 30 Hz. Each sector of the head display 75 has a window display stack 77a–77h of the type shown in FIG. 4.

A window of 24 reliable samples will be continuously updated. As the 25th sample is obtained, the first is dropped out of the window, as the 26th is obtained, the 2nd is dropped, etc. For each feature in every derivation, $M+\sigma$ are continuously updated across the most recent 24 samples. This will be referred to as a "continuously updated norm". As soon as the first such set of norms is defined from the first 24 samples, a t-test will be performed between each subsequent segment and the previous 24, using the current values of M and $\sigma$. If a significant difference is detected, *the window stops being updated.* The values of M and $\sigma$ are stored and a new window begins to be constructed, accumulating the next 24 samples. Each sample continues to be t-tested against M and $\sigma$ of the window up to the point of detected instability or change. Each segment t-test result is reported separately. When the full new window of 24 samples has been gathered, a t-test is performed between the window before change was detected (NORM n) and the current window (NORM n+1). If the two windows are significantly different, the visual alarm 82 will be lighted or a buzzer 83 will sound.

The storage registers 84a–84h stores the updated window norms (NORM n) and (NORM n+1) corresponding to the window. An updated norm can be constructed at any time and stored. This might be used to construct an updated self-norm for every stage within a CPB procedure, such as a change in pump flow rate or perfusion fluid temperature.

Figure 5:
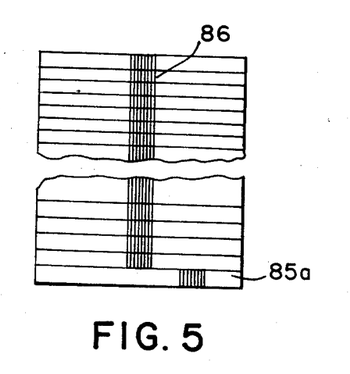
FIG. 5 is a front plan view illustrating a similar spectral array under a different set of conditions.

As an example, assume the 25th sample is significantly different from the 24 previous samples in the window. The 24 lines of the stack 85x–85b, corresponding to the 24 samples of the window, are replaced by one line 86 representing the average values of the previous 24 line window, as shown in FIG. 5. The new line 85a, significantly different, appears below the previous window average. The software window stops continuously updating and a new window is opened with the significant finding as the first line below the average of the previous window. That head sector begins to "blink" once per second. Successive samples are compared to the previous window norms, "NORMS"$_n$. If the difference is not significant, the blinking stops. If it is significant, the blinking resumes. When the full new set of 24 reliable samples fills the window, a formal test of significance is performed between NORMS$_n$ and NORM$_n$+1, constructed from the M and $\sigma$ of features in the last 24 samples. If the two sets of data are significantly different at the selected p-value, a visual alrm 96, or auditory alarm, will inform the operator.

The operator may expect the state change which has been detected because of a known deliberate clinical maneuver, e.g., change in pump flow rate. He may then elect to replace the previous NORMS$_n$, as more appropriate, by operation of switch 87. He may wish to compare the new NORMS$_n$+1 to some other baseline, such as "postanesthesia self norms", before making a decision. A switch 88 on the panel would select a prior alternative norm set and appropriately report this on the head display. He may not have been previously aware of the change in state, institute a corrective procedure, and watch the state change back until it is no longer different from NORMS$_n$ (this implies NORMS$_n$+2 will not be different from NORMS$_n$).

In this embodiment a "spike detector", for each sector, may be a small square which will blink to indicate the presence of spikes in that sector, as shown at 89 in FIG. 3.

C. Alternative Simplified Display of Windows of Norms

Figure 6:
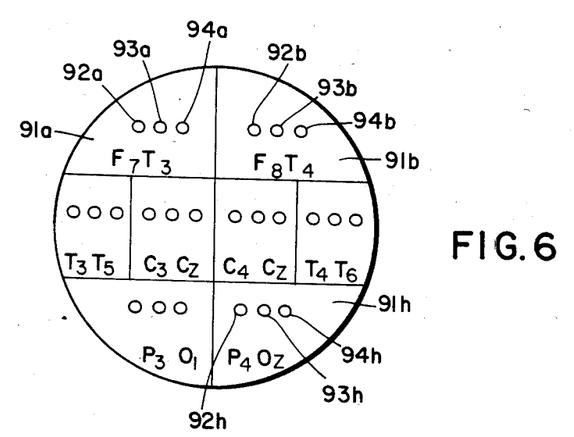
FIG. 6 is an illustration of a portion of the display panel of an alternative embodiment.

A further alternative embodiment is shown in FIG. 6 to replace the spectral arrays 75 of FIG. 3. In this embodiment the analysis and comparison associated with the moving window is the same; however, the results are displayed in a simplified form. The head diagram 90 is divided into eight sectors 91a–91h, each of which has three color-coded lights, for example, LED's; preferably green 92a–92h; amber 93a–93h; and red 94a–94h. In each sector green lights, when lighted, would indicate that the comparison shows no meaningful difference; an amber light when lighted would indicate that the latest sample (most recently taken sample) was significantly different from the average of the samples (for example 24) of the prior window; and the lighting of a red lamp would indicate that the two windows (NORM$_n$) and (NORM$_n$+1) are significantly different.

D. Alarms

During an operation a comparison is made between the current sample and the rest of previous (current) window and norms. (1) If significance threshold exceeded, an "alert" state is entered (amber light or sector outlined in red); (2) The sliding window collapses into M and $\sigma$ across previous n segments in sample; (3) New window (group) is constructed, with each segment tested against M and $\sigma$ from previous group. The alert is maintained or reversed; (4) If the alert is maintained, a t-test is performed between window N and N+1.

If the t-test shows that the difference between N and N+1 is significant, an alarm light 60 will be lighted, or alternatively a buzzer will sound. Preferably, a different warning light 61 is used to alert that the calibration of the differential amplifiers is unsatisfactory. The warning lights of the panel of lights 57 warns that the impedance of the electrodes is unsatisfactory, with each light on the panel 57 corresponding to an electrode, see FIG. 3. For the "alert" state the amber light is shown in FIG. 6 and the sector outlined in red is shown in FIG. 3.

A PROGRAMMED KEYBOARD AND USER OPTIONS

Figure 7:
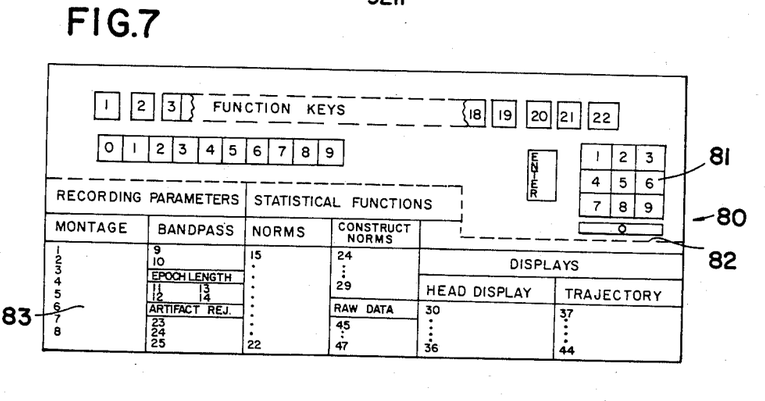
FIG. 7 is an illustration of an additional control panel which may be used in connection with the control and display panel of FIG. 3.

In FIG. 7 an additional control panel (keyboard) is illustrated which has a number of programmed keys (function keys). Each such key, which is labeled with its function, when activated, will call up a small control program from the microprocessor's memory and effectuate the program. The "enter choice" key may be the normal "return" key of the microprocessor. For example, when the key F1 "calibrate amplifiers" is depressed the program will in turn caliberate each of the differential amplifiers, as explained above.

The system is "menu driven" i.e. before the acquisition and analysis data begins the user must select from a series of options from a "menu", i.e., list, displayed on the CRT screen 75. The menu options are discussed in detail below. But, for example, when the user operates function key F9, which constructed a norm, the norm has been pre-selected by the user from the menu. So when the user operates function key F9 the norm constructed may be, for example, the self-norm for the patient when pre-operative and conscious. The operation of the function key F9 will automatically begin the construction (data collection and analysis) for that norm.

The following is the preferred "menu". Each group provides a choice of options. For example, under "Bandpass" (frequency range) the user may select "9" or "10" which provides 1-50 Hz or 1-100 Hz respectively. The user will select one or the other, before the data is started to be collected, by depressing "9" or "10" on the numerical key pad 81.

Preferably, 19 of the function keys are programmed as follows:

F1 CALIBRATE AMPLIFIERS
F2 ELECTRODE IMPEDANCE TEST
F3 RECORD EEG (recorded on floppy disk or other recording media)
F4 DISPLAY EEG (8 channels—on line)
F5 DISPLAY SPIKES (their picture, not number)
F6 DISPLAY HEAD PICTURE #X, (type desired #)
F7 DISPLAY TRAJECTORY #X, (type desired #)
F8 CHANGE REFERENCE NORMS TO #X, (type desired #)
F9 CONSTRUCT NORM #X, (type desired #)
F10 DISPLAY t-TEST AGAINST NORM #X,
F11 DISPLAY t-TEST NORM #X vs. NORM #Y,
F12 REPLAY FROM $T_1$ (00:00:00) to $T_2$ (00:00:00)
F13 DISPLAY MENU ON VIDEO
F14 PRINT VIDEO (read out)
F15 BEGIN #X
F16 END #X
F17 DISPLAY [L#X-R#X]
F18 AUTOMATIC RETURN TO BASIC CONDITIONS AFTER TIME LAPSE
F19 AUTOMATIC ALARM

MONTAGE

1 Whole head EEG, 8 channels bipolar (+EKG, BP, RGCP)
2 Left hemisphere, 8 channels monopolar
3 Right hemisphere, 8 channels monopolar
4 Front of head bilateral, 8 channels monopolar
5 Back of head bilateral, 8 channels monopolar
6 Whole head bilateral side, 8 channels monopolar $F_{P1}/F_{P2}$, $F_7/F_8$, $T_3/T_4$, $T_5/T_6$
7 Whole head bilateral middle, 8 channels monopolar $F_3/F_4$, $C_3/C_4$, $P_3/P_4$, $O_1/O_2$
8 Whole head, 16 channel monopolar-optional

| BANDPASS | EPOCHLENGTH | |
|---|---|---|
| 1-50 Hz | 11 | 2.56 sec |
| 1-100 Hz | 12 | 5.12 sec |
| | 13 | 10.24 sec |
| | 14 | 20.48 sec |

NORMS

15 AGE REGRESSION EQUATIONS
16 SELF NORM-PATIENT CONSCIOUS (pre-operative)
17 SELF NORM-PATIENT ANESTHETIZED (pre-operative)
18 PREVIOUS MINUTE, MOVING WINDOW
19 PREVIOUS 5 MINUTES, MOVING WINDOW
20 PUMP-PATIENT RELATIONSHIP, FULL FLOW, 37°
21 PUMP-PATIENT RELATIONSHIP, ACTUAL FLOW AND TEMP
22 SELF-NORM—CONDITION X (STRIKE X ON KEYBOARD)

ARTIFACT REJECTION

23 AMPLITUDE THRESHOLD (STATIC)
24 GAUSSIANITY TEST (DYNAMIC)
25 SUBTRACT CURRENT EKG SPECTRUM (ABSOLUTE POWER) (BEFORE DISPLAY OF DATA)

NORM CONSTRUCTION

24 COMPUTE 'SELF NORM, CONDITION X' WITHIN ANY PATIENT INDICATED BY 'BEGIN 1—END 1', BEGIN 2—END 2, ETC.
25 STORE RESULT OF 24 ON POPULATION DISK OR SESSION DISK
26 COMPUTE MEANS+SD ACROSS TOTAL SAMPLE ON POPULATION DISK—'POPULATION NORM, CONDITION X'
27 DISPLAY MATRIX 24
28 DISPLAY MATRIX 26
29 STORE RESULT OF 26 ON PROGRAM DISK, IDENTIFIED AS POPULATION MORM, CONDITION X EKG, EP, RESP DIGITAL DISPLAY ON TOP OR BOTTOM

DISPLAY SELECTION—HEAD PICTURES

30 DENSITY CODED SPECTRAL ARRAY, ABSOLUTE POWER
31 DENSITY CODED BAND ARRAY, ABSOLUTE POWER
32 DENSITY CODED SPECTRAL ARRAY, RELATIVE POWER
33 DENSITY CODED BAND ARRAY, RELATIVE POWER
34 DENSITY CODED Z-TRANSFORMED BAND ARRAY
35 T-TEST CONDITION X vs. CONDITION Y (DENSITY CODED)
36 T-TEST PRESENT SAMPLE AGAINST NORM X (KEY STRIKE APPROPRIATE NORM KEY OR X)

Select A or B
(A) actual values
(B) Z-values

TRAJECTORIES ]either samples or sessions]

37 DELTA ABSOLUTE POWER, 8 CHANNEL, UPDATING
38 DELTA RELATIVE POWER (%), 8 CHANNEL, UPDATING
39 THETA ABSOLUTE POWER, 8 CHANNEL, UPDATING
40 THETA RELATIVE POWER, 8 CHANNEL, UPDATING
41 ALPHA ABSOLUTE POWER, 8 CHANNEL, UPDATING
42 ALPHA RELATIVE POWER, 8 CHANNEL, UPDATING
43 BETA ABSOLUTE POWER, 8 CHANNEL, UPDATING
44 BETA RELATIVE POWER, 8 CHANNEL, UPDATING

RAW DATA

45 SHOW CURRENT EEG SAMPLE+EKG, BP, RESP
46 SHOW SPIKES DETECTED IN CURRENT SAMPLE
47 SHOW EKG AT BOTTOM OF HEAD OR TRAJECTORY

For example, the user may select the following options, by operating the named keys, which are typical for an intra-operative procedure:

Key 6 (whole-head bilateral side); key 10 (1–100 Hz bandpass); key 13 (10.29 second epochlength); key 18 (previous minute, moving window); 24 (Gaussianity test for artifact rejection); 25 (store result on session disk); 33 (density coded band array, realtive power); 38 (Delta relative power); 50 (heads display).

This will give a moving window display, artifact-free, of Delta relative power.

As shown in FIG. 7, preferably the additional control panel 80, which may be based on a microcomputer keyboard having function keys, only has the function keys (22 function keys) and numerical keyboard 81 (10 keys) readily available to the user. The readily available portion is shown by the dash-dash line 82. The other portion of the keyboard is covered by a hinged cover 83 which has the options 1–36, set forth above.

What is claimed is:

1. An electroencephalograph (EEG) system which is used intra-operatively in open-heart surgery in which the patient's blood is pumped and oxygenated by a cardiovascular bypass, including perfusion blood flow means and perfusion blood temperature means to respectively measure the patient's blood flow and temperature in the cardiovascular bypass and produce respective corresponding signals;

brain wave signal means comprising a series of electrodes adapted to be connected to the patient's head to produce signals representing the patient's brain waves, amplifiers connected to the electrodes, and analog/digital conversion means connected to the amplifiers to produce sets of digital data corresponding to the patient's brain waves from a plurality of sectors of the patient's head;

data analysis means connected to said blood flow means and said blood temperature means and said brain wave signal means to analyze the digitized brain wave signals based upon the following relationship which predicts the neurophysiological processes attributable to biophysical changes which occur with changes in said flow and temperature:

$$\% \text{ change: } A\left[\frac{T_N - T_P}{10}\right] + B\left[\frac{V_N - V_P}{V_N}\right]$$

where $T_N$ is the normal body temperature, $T_P$ is the perfusion blood temperature, $V_N$ is the normal perfusion volume, $V_P$ is the current cardiovascular perfusion volume, A is a coefficient in the range of 0.4–0.6 and B is a coefficient in the range of 0.3–0.5.

2. An electroencephalograph system as in claim 1 wherein A is 0.5.

* * * * *